United States Patent [19]

Thompson et al.

[11] 4,335,115

[45] Jun. 15, 1982

[54] ANTI-ACNE COMPOSITION

[75] Inventors: Edward D. Thompson; Stephen B. Carter, both of Cincinnati; Gary L. Manring, Oxford, all of Ohio

[73] Assignee: The Procter & Gamble Company, Cincinnati, Ohio

[21] Appl. No.: 842,767

[22] Filed: Oct. 17, 1977

Related U.S. Application Data

[63] Continuation of Ser. No. 737,315, Nov. 1, 1976, abandoned.

[51] Int. Cl.³ .............................................. A61K 31/71
[52] U.S. Cl. .................................................... 424/181
[58] Field of Search ........................................ 424/181

[56] References Cited

U.S. PATENT DOCUMENTS 3,535,422 10/1970 Cox et al. ............................. 424/164
4,056,611 11/1977 Young ................................... 424/62

OTHER PUBLICATIONS

Fulton–Topical Therapy for Acne; Arch. Dermatol., 110, 83–86, (1974).
McCutcheon's Detergents and Emulsifiers, 1973, pp. 6–7.
Merck Index, 8th ed., pp. 590–591, (1968).

*Primary Examiner*—Leonard Schenkman
*Attorney, Agent, or Firm*—Rose Ann Dabek; Jerry J. Yetter; Michael J. Roth

[57] ABSTRACT

Compositions for topical application of erythromycin and derivatives or erythromycin comprising ethanol, isopropyl myristate, glycerol monooleate and the erythromycin compounds are especially useful as a treatment for acne.

2 Claims, No Drawings

ANTI-ACNE COMPOSITION

This is a continuation of application Ser. No. 737,315, filed Nov. 1, 1976, now abandoned.

BACKGROUND OF THE INVENTION

This invention relates to compositions for topical application of erythromycin or erythromycin compounds. The compositions herein are particularly useful for the treatment of acne.

*Acne vulgaris* and other types of acne and acneiform skin maladies associated with the hyperplasia of the sebaceous follicle are often treated by the oral administration of antibiotics. Tetracycline has been the traditional drug of choice, but other antibiotics such as erythromycin, lincomycin and clindamycin have also been prescribed for this use. While oral administration of these drugs is often effective in treating acne, oral therapy has several disadvantages. For example, the oral administration of antibiotics subjects the entire body to the antibiotic composition; yet, in acne, only the skin is affected. Moreover, almost all antibiotics have some undesirable side effects when taken orally.

In contrast with oral dosing in the treatment of acne, topical application of antibiotics delivers the antibiotic to the afflicted situs and minimizes the antibiotic levels in the circulatory and gastrointestinal systems. Undesirable side effects occurring from oral administration of the drug are greatly reduced, and yet, properly administered, the therapeutic effect of topical application is comparable with, or superior to, that derived by oral administration.

Compositions for topical treatment of acne are known. Smith, U.S. Pat. No. 3,952,099, issued Apr. 20, 1976, discloses compositions for treating acne lesions by topical application of tetracycline antibiotics in a skin penetration vehicle comprising sucrose monooleate, decyl methyl sulfoxide and alcohol.

Stoughton, U.S. Pat. No. 3,969,516, issued July 13, 1976, and *Arch. Dermatol.*, 84 182 (1976), discloses a method for topically treating acne by applying formulations containing various antibiotics in N-methyl-2-pyrrolidone. The data presented are said to indicate that tetracycline in a pyrrolidone-based penetrating vehicle does not effectively control the inflammatory lesions of acne. In addition to tetracycline, compositions of erythromycin, erythromycin derivatives and clindamycin in the same vehicle were studied. The combination of erythromycin and N-methyl-2-pyrrolidone gave results which were better than tetracycline in the same vehicle, whereas the antibiotic lincomycin gave superior results in controlling the inflamed lesions.

In light of the foregoing, it is clear that the effectiveness of any particular antibiotic as a topical treatment of acneiform skin diseases depends significantly upon the particular skin penetrating vehicle with which it is used.

It is an object of this invention to provide a topical formulation to enhance the penetration of erythromycin and erythromycin compounds through skin.

It is another object of this invention to provide erythromycin compositions which can be used topically in the treatment of "acne", especially *Acne vulgaris*.

It is still another object of this invention to provide storage-stable compositions comprising erythromycin antibiotics in a skin-penetrating vehicle which is especially adapted for the topical treatment of acne.

These and other objects of this invention are secured, as will be seen from the following disclosure.

SUMMARY OF THE INVENTION

The present invention encompasses an antimicrobial composition for topical application, comprising:

(1) a safe and effective amount of an antibiotic agent selected from the group consisting of erythromycin and compounds of erythromycin; and (2) a pharmaceutically acceptable penetrating carrier, comprising (a) from about 0% to about 5% glycerol monooleate;

(b) from about 20% to about 80% ethanol; and (c) the balance comprising isopropyl myristate.

The invention also encompasses methods for treating acne and acneiform skin diseases by topically applying a safe and effective amount of the foregoing type of composition to the afflicted situs.

DETAILED DESCRIPTION OF THE INVENTION

This invention relates to antibiotic compositions especially adapted for the treatment of *Acne vulgaris* and other acneiform skin diseases. The compositions herein comprise a safe and effective amount of erythromycin and/or compounds of erythromycin and a pharmaceutically acceptable penetrating carrier comprising ethanol, isopropyl myristate and, preferably, glycerol monooleate. The method for treating acne comprises the topical application of compositions of the foregoing type to the afflicted situs of the skin of the acne sufferer.

By "afflicted situs" is meant the area of the skin which is inflamed, the acne comedones, papules, pustules, and cysts (acne lesions) and the skin immediately surrounding this area.

By "antibiotic agent" is meant erythromycin base and compounds or derivatives of erythromycin. These antibiotic agents can be used alone or in combination in the present compositions.

By "penetrating carrier" is meant a mixture of ethanol and isopropyl myristate, and, preferably, glycerol monooleate. Other materials which will not interfere with the penetrating action caused by the carrier can be present, and include perfumes, coloring agents and gelling agents to make the carrier aesthetically pleasing. The "penetration" effected through the use of the carrier of this invention can be observed, for example, by measuring the amount of diffusion of the antibiotic agent through skin using a diffusion cell apparatus, as disclosed hereinafter.

By "pharmaceutically acceptable" is meant that the ingredients are suitable for use in contact with the skin and tissues of humans and lower animals without any untoward physiological response, commensurate with a reasonable benefit/risk ratio.

By "safe and effective amount" is meant an amount which is effective to alleviate the inflammation and the lesions of the acne or acneiform skin disease and yet cause no undesirable side effects (at a reasonable benefit/risk ratio). For topical application, a dose range of antibiotic composition of from about 0.1 mg/cm$^2$ per day to about 25 mg/cm$^2$ per day is effective. The dosage can vary from patient to patient, depending on such factors as the severity of the acne, the frequency of application, the area of the body which is afflicted, and the particular erythromycin compound being applied.

By "topical application" is meant directly spreading or laying on epidermal tissue. The application can be made by rubbing, using medicated pads, or by any other convenient means.

By "erythromycin" is meant erythromycin base produced by the strain of *Streptomyces erythreus.* The term includes both erythromycin base and/or its hydrated crystals. By the term "compounds of erythromycin" is meant the salts between erythromycin base and acids, as well as the ester derivatives of erythromycin. Nonlimiting examples of compounds of erythromycin include: erythromycin estolate, which is the lauryl sulfate salt of the propionic acid ester of erythromycin; erythromycin glucoheptonate, which is the glucoheptonic acid salt of erythromycin; erythromycin lactobionate, which is prepared from erythromycin base and lactobiono-δ-lactone; erythromycin propionate, the propionic acid ester of erythromycin; erythromycin stearate, which includes both the stearic acid salt of erythromycin and the stearic acid ester of erythromycin; and erythromycin ethyl succinate, which is the ester of erythromycin and ethyl succinic acid.

By "glycerol monooleate" (also known in the literature as "monoolein") is meant the mono-ester of glycerine and oleic acid. Glycerol monooleate employed herein can be made by any of a number of methods well known in the chemical arts. The predominant product of these reactions is 1-glycerol monooleate, the balance comprising 2-glycerol monooleate. The presence or absence of minor amounts of 2-glycerol monooleate does not appear to have any adverse effect on the penetrating ability of the instant compositions.

By "comprising" is meant that various other compatible ingredients may be present in the compositions in such a proportion as will not adversely affect the stability and penetrating effectiveness of the basic composition. The term "comprising" thus encompasses and includes the more restrictive terms "consisting" and "consisting essentially of" within its scope.

All percentages are by weight, unless otherwise specified herein.

SKIN PENETRATION TESTING

The problems encountered in the topical administration of antibiotics have been the stability of the drug in the carrier or vehicle and the development of a system which allows the drug to penetrate the skin, thus facilitating the delivery of the antibiotic. The selection of the appropriate carrier for an antibiotic agent is critical. Not all delivery systems and penetrating aids will facilitate the diffusion of a given antibiotic agent through the skin barrier. The penetrating carrier must be compatible with the antibiotic; it must be non toxic; and the formulation must be stable.

In order to determine the best penetrating carrier for erythromycin and derivatives of erythromycin, a diffusion study was carried out using the skin of hairless mice. Briefly, the study employed mouse skin which was placed in a vertical position between two capped diffusion cells. A potassium phosphate buffer at pH 8 was added to the diffusion cell abutting the subcutaneous side of the mouse skin and the test composition comprising a solution of the antibiotic agent and the penetrating carrier was added to the diffusion cell abutting the epidermal side of the mouse skin. A small glass bead was added to each diffusion cell to provide mixing.

This cell assembly was arranged in an oscillating water bath at about 31° C. The diffusion time used for the test was about 20 to 24 hours.

At the end of this time period, each diffusion cell assembly was removed from the water bath, and the diffusate from the cell abutting the subcutaneous side of the skin was filtered by expressing the liquid through a disposable filter attached to a plastic disposable syringe. This diffusate was then submitted for microbiological agar diffusion assay done in accordance with the procedure described at 21 C.F.R. 436.105. This test provides a measure of the passage of active erythromycin antibiotic through the skin.

Table 1 lists a representative number of penetrating carriers and their activity, as micrograms erythromycin which penetrated through the mouse skin, per milliliter (μg/ml) of diffusate.

TABLE 1

| | | Penetration Data (hairless mouse skin) | | | |
|---|---|---|---|---|---|
| Alcohol | Ester | Optional Penetration Enhancers | Water | Erythromycin | Activity (μg erythromycin/ml) |
| 48% ethyl | 50% isopropyl myristate | | | 2% | 2175 |
| 28% ethyl | 70% isopropyl myristate | | | 2% | 2915 |
| 40% ethyl | 53% isopropyl myristate | 3% glycerol monooleate | | 4% | 1563 |
| 38.4% ethyl | 57.6% isopropyl myristate | 2% glycerol monooleate | | 2% | 1685 |
| 60% ethyl | | 2% glycerol monooleate | 34% | 4% | 750 |
| | 98% isopropyl myristate | | | 2% | 36.5 |
| 20% ethyl 40% isopropyl | | 3% glycerol monooleate | 35% | 2% | 140 |
| 56% ethyl | 38% diisopropyl adipate | 2% glycerol monooleate | | 4% | 247 |
| 75.2% ethyl | 18.8% triethyl citrate | 2% glycerol monooleate | | 4% (ethylsuccinate) | 174 |
| 57.9% ethyl 9.7% 2,2-dimethyl-1,3-dioxolene-4-methanol | 29% isopropyl myristate | 1.5% glycerol monooleate | | 2% | 407 |
| 73% ethyl 25% propylene glycol | | 0.1% decylmethyl sulfoxide | | 2% | 5.6 |
| 59% ethyl | | 0.1% decylmethyl sulfoxide | 39% | 2% | 7.3 |
| 58% ethyl | | 0.1% decyl- | 39% | 2% | 15.3 |

TABLE 1-continued

| | | Penetration Data (hairless mouse skin) | | | |
|---|---|---|---|---|---|
| Alcohol | Ester | Optional Penetration Enhancers | Water | Erythromycin | Activity (μg erythromycin/ml) |
| 70% isopropyl 25% propylene-glycol | | methyl sulfoxide 0.1 sucrose esters 3% oleic acid | 2% | | 8.3 |

As can be seen from the data, the selection of the penetrating carrier for erythromycin is quite critical. Of the combinations tested, mixtures of isopropyl myristate and ethanol exhibited by far the best penetration characteristics. Furthermore, the ratio of the isopropyl myristate to ethanol was also found to be critical. However, to ensure the solubility of the erythromycin or its compounds in the formulation, it is necessary to maintain a balance between the isopropyl myristate and ethanol. A mixture of about 20% to about 80% isopropyl myristate with about 20% to about 80% ethanol is acceptable. A preferred mixture comprises from about 45% to about 60% isopropyl myristate and from about 30% to about 45% ethanol; a highly preferred mixture consists essentially of about 60% isopropyl myristate and about 40% ethanol.

The foregoing data indicate that erythromycin and compounds of erythromycin when used in a carrier comprising ethanol and isopropyl myristate are very effective in penetrating the epithelium of excised hairless mouse skin. Moreover, the data indicate that materials which are known to be excellent penetrants for tetracycline are not particularly useful with erythromycin.

A second study similar to that using the mouse skin was conducted using human abdominal skin, in an in vitro model. The test system consisted of a sampling cell and a skin sample in contact with a collection cell containing a phosphate buffer at pH 8. The skin surface was treated with the formulation four times during an 8 or 24 hour period. The sample cell was arranged in a water bath at 31° C. At the end of the treatment, the phosphate buffer was removed from the collection cell and subsequently analyzed for the amount of erythromycin present.

Table 2 summarizes the data from this study. The results demonstrate that glycerol monooleate greatly enhances the penetration of the erythromycin through human skin. Accordingly, erythromycin formulations containing glycerol monooleate, ethanol and isopropyl myristate are superior for human skin penetration.

45% ethanol, about 1% to about 5% glycerol monooleate, and the remainder being isopropyl myristate. It is necessary that the glycerol monooleate be limited to an amount less than 5% because above that concentration glycerol monooleate can cause minor skin irritation.

In addition to using erythromycin base as the antimicrobial agent in the above topical formulations, other erythromycin compounds or derivatives can be used. A preferred erythromycin derivative is erythromycin ethylsuccinate. Other compounds which can be used are erythromycin propionate, erythromycin stearate, erythromycin lactobionate, erythromycin glucoheptonate, and erythromycin propionate lauryl sulfate. In addition, mixtures of these compounds can also be used. The limiting factor in the choice of the erythromycin antibiotic is the solubility and the stability of the compound in the ethanol, isopropyl myristate, glycerol monooleate penetrating carriers.

Water can be present in the compositions of this invention without deleteriously affecting the penetration of the antibiotic. However, the presence of large amounts of water causes the erythromycin and erythromycin compounds to become unstable on prolonged storage. The preferred compositions of this invention are substantially water-free, i.e., they contain less than about 5% water.

The preferred acne treatment of this invention comprises applying safe and effective amounts of the topical composition to the afflicted situs on the skin. An effective dosage is about 0.1 mg/cm$^2$ to about 25 mg/cm$^2$ of the antibiotic composition per day. It is preferred to cleanse the skin prior to treatment, and any soap or detergent composition suitable for washing the skin can be employed. The treatment is more effective if the topical applications are made 2 to 4 times per day.

In a method aspect of this invention, the afflicted situs (the acne lesions and surrounding inflamed area) is treated by applying thereto a safe and effective amount of an anti-acne composition comprising:

(1) from about 0.1% to about 10% of an antibiotic selected from the group of erythromycin and com-

TABLE 2

| | | Penetration Data (human skin) | | | |
|---|---|---|---|---|---|
| Ethyl Alcohol | Isopropyl Myristate | Glycerol Monooleate | Water | Erythromycin | Activity (μg/ml) |
| 40% | 58% | 0 | 0 | 2% | 1.70* |
| 40% | 56% | 0 | 0 | 4% | 1.15* |
| 50% | 0 | 0 | 48% | 2% | 0.51* |
| 40% | 55% | 3% | 0 | 2% | 6.55* |
| 40% | 55% | 3% | 0 | 2% | 5.50** |
| 40% | 54% | 2% | 0 | 4% | 5.84** |
| 50% | 0 | 2% | 46% | 2% | 0.82** |
| 40% | 56% | 0 | 0 | 4% | 1.87** |
| 40% | 48% | 0 | 0 | 2% | 0.38** |

*24 hour study
**8 hour study

The preferred carrier for topical application to human skin is a mixture of from about 30% to about pounds of erythromycin; and (2) a pharmaceutically acceptable penetrating carrier comprising:
(a) from about 0% to about 5% glycerol monooleate;
(b) from about 20% to about 80% ethanol; and
(c) the balance comprising isopropyl myristate.

In a preferred method, the composition comprises:
(1) about 2% to about 5% erythromycin;
(2) about 1% to about 5% glycerol monooleate;
(3) about 30% to about 45% ethanol; and
(4) about 45% to about 60% isopropyl myristate.

The following examples are intended to illustrate typical antibiotic compositions of this invention, but are not intended to be limiting thereof. All materials used in the compositions are commercially available, or can be prepared in the manner described herein.

In a preferred method of preparation of glycerol monooleate, about 3 moles of methyl oleate are admixed with about 11 moles of anhydrous glycerine and about 22 moles of dimethyl acetamide (solvent) containing 80 ml of a 10% slurry of sodium methoxide and 80 ml xylene. The mixture is heated to about 100° C. at 80 mm mercury, with stirring, for two hours. The product of this reaction is predominately (ca. 90% or greater) the 1-glycerol monooleate, the balance comprising 2-glycerol monooleate and non-interferring reactants and by-products.

The following examples employ absolute ethanol. Both absolute (100%) and 95% ethanol are acceptable for the practice of this invention. In the preferred substantially water-free compositions, absolute ethanol is used. Denatured ethanol can be used so long as the denaturant is pharmaceutically acceptable and does not adversely affect the antibiotic or penetrating characteristics of the carrier.

The compositions herein can also include various agents and ingredients commonly employed in dermatological and cosmetic ointments and lotions. For example, perfumes, gelling and thickening agents such as carboxymethyl cellulose, ethyl cellulose, coloring agents and the like, can be present in the compositions to provide a more pleasing aesthetic aspect.

EXAMPLE I

| Ingredient | Percent (wt.) |
| --- | --- |
| Erythromycin base | 4% |
| Glycerol monooleate | 3% |
| Ethanol | 40% |
| Isopropyl myristate | Balance |

The above ingredients are blended mechanically and provide a fluid composition adapted for topical application to skin. The composition of Example I enhances the penetration of the erythromycin base into and through skin, and is especially useful in the treatment of *Acne vulgaris*.

A person afflicted with acne lesions is treated by topically applying the composition of Example I to the acne lesions at a rate of 3 mg/cm$^2$ of antibiotic composition twice a day for 6 weeks. At the end of this period, there is a substantial reduction in the number of acne lesions and the inflammation is reduced.

Erythromycin ethylsuccinate is substituted for the erythromycin base of Example I and similar results are obtained.

EXAMPLE II

| Ingredient | Percent (wt.) |
| --- | --- |
| Erythromycin base | 2% |
| Glycerol monooleate | 2% |
| Ethanol | 40% |
| Ethyl cellulose | 10% |
| Isopropyl myristate | Balance |

The above composition provides a creamy gel base adapted to topical application to skin which can be packaged in a roll-on bottle. This composition enhances the penetration of the erythromycin base into and through human skin, and is an excellent topical treatment for acne when used regularly, per the treatment regimen of Example I.

When erythromycin ethylsuccinate is substituted for the erythromycin of Example II, similar results are obtained.

EXAMPLE III

| Ingredient | Percent (wt.) |
| --- | --- |
| Erythromycin base | 4% |
| Ethanol | 40% |
| Isopropyl myristate | Balance |

The above ingredients are mechanically blended and a fluid product which is suitable for enhancing the penetration of erythromycin into and through animal tissue is provided. The composition is used twice daily in the topical treatment of acne.

In the composition of Example III, the erythromycin base is replaced by an equivalent amount of erythromycin propionate and erythromycin stearate, respectively, and equivalent results are secured.

EXAMPLE IV

| Ingredient | Percent (wt.) |
| --- | --- |
| Erythromycin ethylsuccinate | 4% |
| Ethanol | 45% |
| Glycerol monooleate | 2.5% |
| Coloring agents | 1% |
| Clay | 1 to 1.5% |
| Isopropyl myristate | Balance |

The coloring agents in the above formulation are blended to provide a flesh colored formulation. The above ingredients are then mixed and provide a flesh-toned cosmetic cream which enhances the penetration of the erythromycin ethylsuccinate through and into the acne lesion and inflamed tissues around the lesion. The cosmetic base acts as a cover-up for the afflicted situs during treatment.

What is claimed is:
1. A water-free antimicrobial composition for topical application which consists essentially of:
(1) from about 2% to about 5% erythromycin;
(2) from about 1% to about 5% glycerol monooleate;
(3) from about 30% to about 45% ethanol; and
(4) about 45% to about 60% isopropyl myristate.
2. A method of treating acne topically by applying to the afflicted situs a safe and effective amount of a composition comprising:
(1) from about 2% to about 5% erythromycin;
(2) from about 1% to about 5% glycerol monooleate;
(3) from about 30% to about 45% ethanol; and
(4) from about 45% to about 60% isopropyl myristate.

* * * * *